(12) United States Patent
Thompson

(10) Patent No.: US 11,692,992 B1
(45) Date of Patent: Jul. 4, 2023

(54) HOUSING FOR FLEXIBLE FUEL SENSOR AND METHOD OF USE

(71) Applicant: Bryan Thompson, Fort Worth, TX (US)

(72) Inventor: Bryan Thompson, Fort Worth, TX (US)

( * ) Notice: Subject to any disclaimer, the term of this patent is extended or adjusted under 35 U.S.C. 154(b) by 0 days.

(21) Appl. No.: 17/824,538

(22) Filed: May 25, 2022

Related U.S. Application Data

(63) Continuation of application No. 17/345,884, filed on Jun. 11, 2021, now Pat. No. 11,360,071.

(51) Int. Cl.
*G01D 11/24* (2006.01)
*G01N 33/28* (2006.01)

(52) U.S. Cl.
CPC ....... *G01N 33/2852* (2013.01); *G01D 11/245* (2013.01)

(58) Field of Classification Search
CPC .......... G01D 11/245; G01N 33/2852
See application file for complete search history.

(56) References Cited

U.S. PATENT DOCUMENTS

| | | | | |
|---|---|---|---|---|
| 2005/0188961 A1* | 9/2005 | Devall | ............... | F02M 31/205 123/541 |
| 2005/0279131 A1* | 12/2005 | Battiste | ............... | F25J 1/0022 62/611 |
| 2008/0282779 A1* | 11/2008 | Noguchi | ............... | G01N 21/15 73/53.01 |
| 2018/0340485 A1* | 11/2018 | Di Gennaro | ........... | F02B 37/04 |

* cited by examiner

*Primary Examiner* — Jamel E Williams
(74) *Attorney, Agent, or Firm* — Leavitt Eldredge Law Firm

(57) ABSTRACT

A housing for a flexible fuel sensor and method of use is disclosed. The housing comprises of a first chamber, a second chamber, and bypass passageway extending therebetween. The first chamber is configured to receive and hold the first conduit of the flexible fuel sensor. The second chamber is configured to receive and hold the second conduit of the flexible fuel sensor. The bypass passageway is configured to permit fuel to flow therethrough and thereout.

2 Claims, 3 Drawing Sheets

HOUSING FOR FLEXIBLE FUEL SENSOR AND METHOD OF USE

BACKGROUND

1. Field of the Invention

The present invention relates generally to flexible fuel vehicle systems, and more specifically to a housing for a flexible fuel sensor that allows higher volume of fuel to flow through the flexible fuel sensor.

2. Description of Related Art

Flexible fuel vehicle systems are well known in the art and are effective means for operating internal combustion engines on fuel comprising of gasoline or any blend of gasoline and ethanol. For example, FIG. 1 depicts a conventional method 101 of flexible fuel vehicle systems, wherein a flexible fuel vehicle initiates performance, as shown with box 103. As fuel flows through a flexible fuel sensor via tubing, the flexible fuel sensor measures the ethanol-gasoline ratio of the fuel, as shown with boxes 105, 107. The flexible fuel vehicle will then adjust its fuel injection based on the ethanol-gasoline ratio of the fuel, as shown with box 109.

One of the problems commonly associated with method 101 is its limited fuel volume flow. For example, when flexible fuel vehicles require high performance, higher volumes of fuel are required to flow to the internal combustion engine. However, the tubing routing fuel through the flexible fuel sensor limits the amount of fuel volume flow. Currently, flexible fuel vehicle systems employ additional tubing to bypass additional fuel around the flexible fuel sensor. Still, the additional tubing takes up space and complicates fuel flow within flexible fuel vehicle systems.

Hence, it would be advantageous to have a system and method that provides for increased fuel volume flow through and around flexible fuel sensors for improved flexible fuel vehicle performance without the use of tubing.

Accordingly, although great strides have been made in the area of flexible fuel vehicle systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
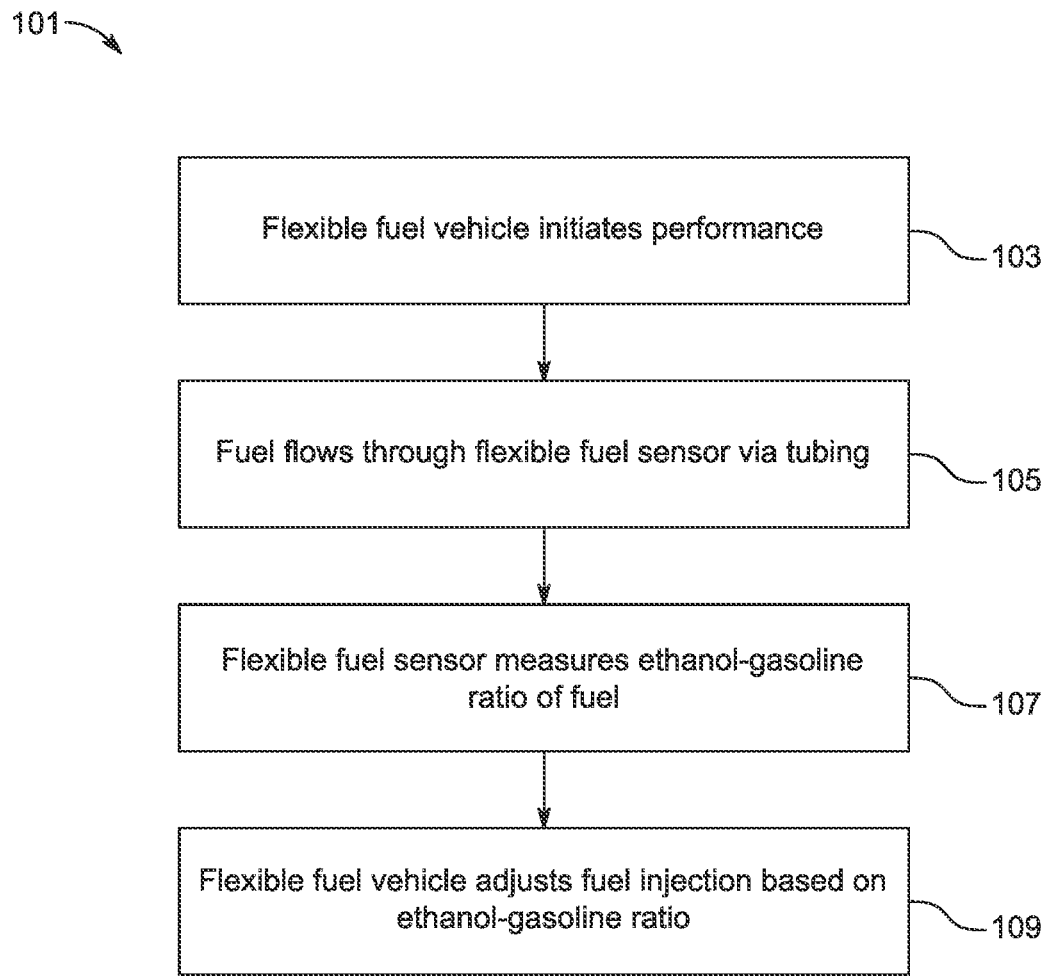
FIG. 1 is a flowchart of a common method of flexible fuel vehicle systems.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional flexible fuel vehicle systems. Specifically, the present invention allows fuel to flow through and around a flexible fuel sensor, thereby allowing larger volumes of fuel to flow through during performance. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
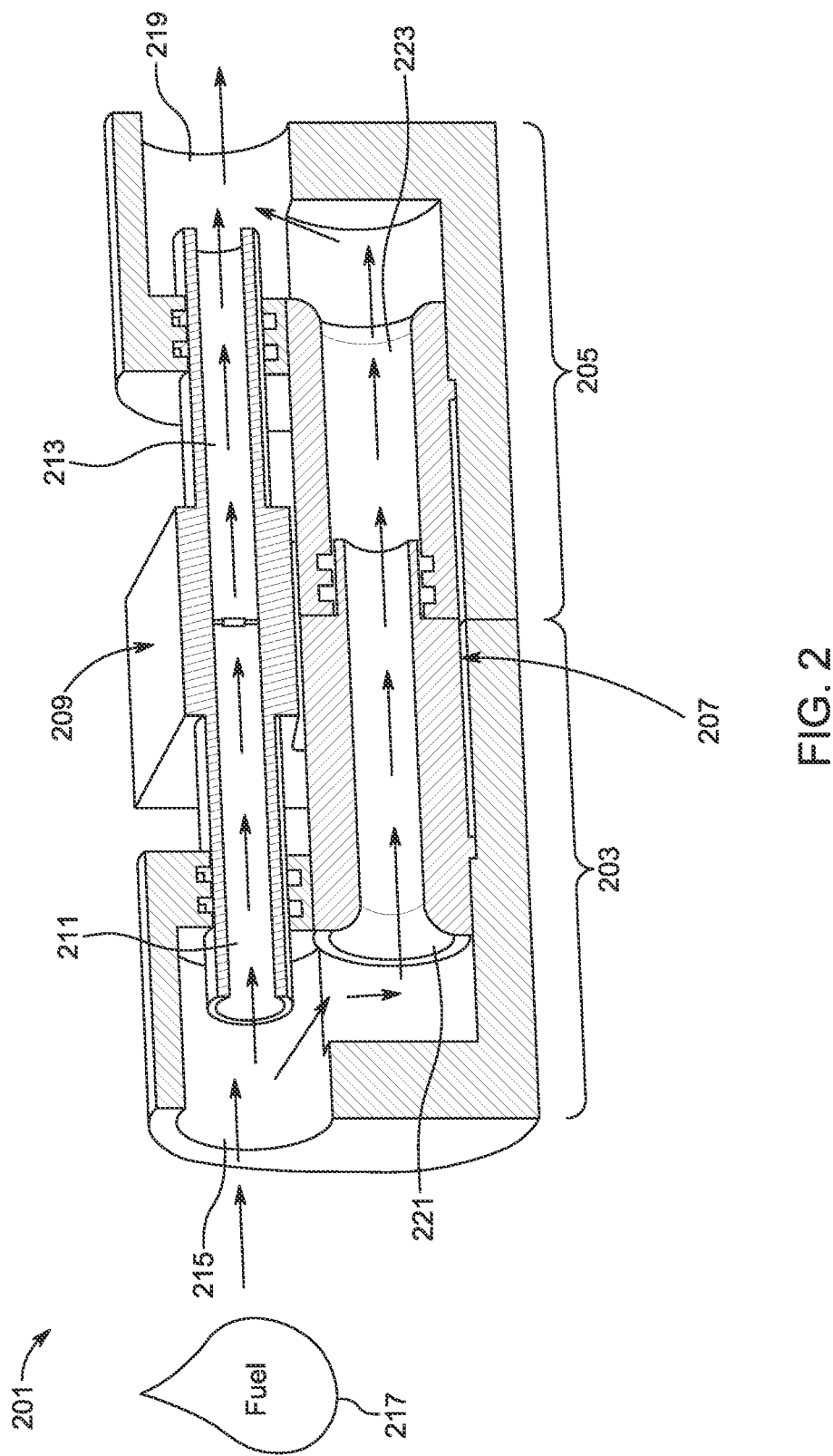
FIG. 2 is a cross-sectional view of a housing for a flexible fuel sensor in accordance with a preferred embodiment of the present invention.

Referring now to the drawings wherein like reference characters identify corresponding or similar elements throughout the several views, FIG. 2 depicts a cross-sectional view of a housing for a flexible fuel sensor 201 in accordance with a preferred embodiment of the present application. It will be appreciated that the housing 201 overcomes one or more of the above-listed problems commonly associated with conventional flexible fuel vehicle systems.

In the contemplated embodiment, the housing 201 comprises of a first chamber 203 and a second chamber 205 with a bypass passageway 207 extending therebetween. it should be appreciated that the housing 201 may vary as functional, manufacturing, or aesthetical considerations require.

The first chamber 203 is configured to receive and hold a first conduit 211 of a flexible fuel sensor 209. In addition, the first chamber 203 includes an inlet 215 configured to permit fuel 217 to flow therethrough.

The second chamber 205 is configured to receive and hold a second conduit 213 of the flexible fuel sensor 209. Additionally, the second chamber 205 includes an outlet 219 configured to permit fuel 217 to flow thereout.

It should be appreciated that the housing 201 securely holds the flexible fuel sensor 209.

It should be appreciated that the first chamber 203 may be integrally formed as part of the second chamber 205, or vice versa, or it may be separately formed and engaged therewith (e.g., by adhesives or cements; by welding, brazing, soldering, or other fusing techniques; by mechanical connectors; etc.).

The bypass passageway 207 includes a first end 221 and a second end 223. The first end 221 is configured to permit fuel 217 to flow therethrough. The second end 223 is configured to permit fuel 217 to flow thereout.

It should be appreciated that the bypass passageway 207 may be integrally formed as part of the first chamber 203, the second chamber 205, or both, or it may be separately formed and engaged with the first chamber 203, the second chamber 205, or both (e.g., by adhesives or cements; by welding, brazing, soldering, or other fusing techniques; by mechanical connectors; etc.).

It should be appreciated that the directional flow of fuel 217 may be reversed through the housing 201. For example, fuel 217 may flow through the outlet 219 and into the second chamber 205. The fuel 217 may then enter the second conduit 213 of the flexible fuel sensor 209 and the second end 223 of the bypass passageway 207. The fuel 217 may then flow into the first chamber 203 via the first conduit 211 of the flexible fuel sensor 209 and the first end of the bypass passageway 207. The fuel 217 may then exit the housing 201 via the inlet 215.

It should also be appreciated that one of the unique features believed characteristic of the present application is the configuration of the first chamber 203 and the second chamber 205 that allow fuel 217 to flow through the flexible fuel sensor 209 and the bypass passageway 207 in a parallel fashion.

Figure 3:
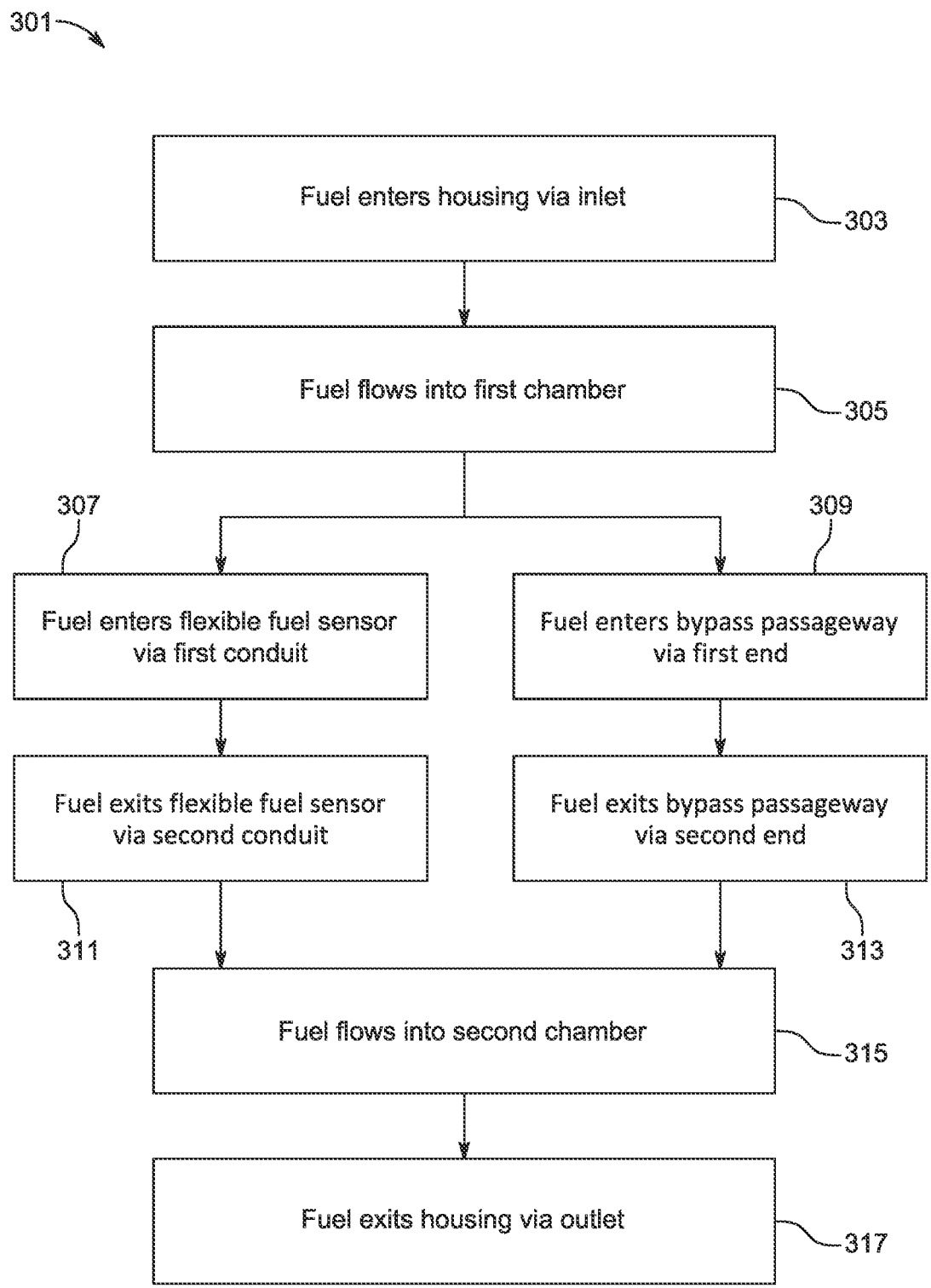
FIG. 3 is a flowchart of a method of operation in accordance with the present application.

In FIG. 3, a flowchart 301 depicts a method of operation in accordance with the present application. When fuel enters the housing via the inlet, fuel flows into the first chamber, as shown with boxes 303, 305. As fuel enters the flexible fuel sensor via the first conduit, fuel enters the bypass passageway via the first end, as shown with boxes 307, 309. Fuel then exits the flexible fuel sensor via the second conduit and the bypass passageway via the second end simultaneously, as shown with boxes 311, 313. Once fuel flows into the second chamber, fuel exits the housing via the outlet, as shown with boxes 315, 317.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A housing for a flexible fuel sensor, comprising:
   a pair of conduits;
   a first chamber configured to receive and hold a first conduit of the pair of conduits of the flexible fuel sensor, the first chamber having an inlet configured to permit fuel to flow therethrough;
   a second chamber configured to receive and hold a second conduit of the pair of conduits of the flexible fuel sensor, the second chamber having an outlet configured to permit fuel to flow thereout; and
   a bypass passageway extending between the first chamber and the second chamber, the bypass passageway having a first end and a second end, wherein the first end is configured to permit fuel to flow therethrough, wherein the second end is configured to permit fuel to flow thereout.

2. A method of improving performance of flexible fuel vehicles, the method comprising:
   providing a housing for a flexible fuel sensor, the housing comprising:
      a pair of conduits;
      a first chamber configured to receive and hold a first conduit of the pair of conduits of the flexible fuel sensor, the first chamber having an inlet configured to permit fuel to flow therethrough;
      a second chamber configured to receive and hold a second conduit of the pair of conduits of the flexible fuel sensor, the second chamber having an outlet configured to permit fuel to flow thereout; and
      a bypass passageway extending between the first chamber and the second chamber, the bypass passageway having a first end and a second end, wherein the first end is configured to permit fuel to flow therethrough, wherein the second end is configured to permit fuel to flow thereout;
   wherein the bypass passageway extends substantially parallel with the pair of conduits of the flexible fuel sensor;
   allowing fuel to enter the housing via the inlet;
   allowing fuel to flow through the first chamber and the second chamber;
   allowing fuel to flow through the flexible fuel sensor; and
   allowing fuel to exit the housing via the outlet.

* * * * *